United States Patent
Batiste et al.

(10) Patent No.: US 8,961,557 B2
(45) Date of Patent: Feb. 24, 2015

(54) INTRAVENOUS FILTER WITH FLUID OR MEDICATION INFUSION CAPABILITY

(71) Applicants: Stanley Batiste, Granite Bay, CA (US); Steven Achstein, Roseville, CA (US)

(72) Inventors: Stanley Batiste, Granite Bay, CA (US); Steven Achstein, Roseville, CA (US)

( * ) Notice: Subject to any disclaimer, the term of this patent is extended or adjusted under 35 U.S.C. 154(b) by 0 days.

(21) Appl. No.: 13/906,254

(22) Filed: May 30, 2013

(65) Prior Publication Data

US 2013/0267914 A1 Oct. 10, 2013

Related U.S. Application Data

(63) Continuation-in-part of application No. 12/012,136, filed on Jan. 30, 2008.

(60) Provisional application No. 61/653,344, filed on May 30, 2012, provisional application No. 60/898,939, filed on Jan. 31, 2007.

(51) Int. Cl.
| | | |
|---|---|---|
| A61F 11/00 | (2006.01) | |
| A61F 2/01 | (2006.01) | |
| A61M 5/165 | (2006.01) | |
| A61M 39/02 | (2006.01) | |

(52) U.S. Cl.
CPC .............. *A61F 2/013* (2013.01); *A61M 5/165* (2013.01); *A61M 39/0247* (2013.01); *A61F 2002/011* (2013.01); *A61F 2002/016* (2013.01); *A61F 2230/0006* (2013.01); *A61F 2230/0091* (2013.01); *A61F 2250/0059* (2013.01); *A61F 2250/0067* (2013.01); *A61M 2039/0205* (2013.01)
USPC ........................................... 606/200; 606/108

(58) Field of Classification Search
CPC ................ A61F 2/0022; A61F 2/0095; A61F 2002/016; A61F 2/143; A61F 2/148
USPC ................................................... 606/200, 108
See application file for complete search history.

(56) References Cited

U.S. PATENT DOCUMENTS

| | | | |
|---|---|---|---|
| 4,494,531 A | 1/1985 | Gianturco | |
| 4,793,348 A | 12/1988 | Palmaz | |
| 5,108,418 A | 4/1992 | Lefebvre | |
| 5,188,616 A | 2/1993 | Nadal | |
| 5,375,612 A | 12/1994 | Cottenceau et al. | |
| 5,707,389 A * | 1/1998 | Louw et al. | 606/200 |
| 6,007,558 A | 12/1999 | Ravenscroft et al. | |
| 6,059,825 A | 5/2000 | Hobbs et al. | |
| 6,267,777 B1 | 7/2001 | Bosma et al. | |
| 6,558,404 B2 | 5/2003 | Tsukernik | |
| 2002/0116024 A1 | 8/2002 | Goldberg et al. | |

(Continued)

*Primary Examiner* — Victor Nguyen
*Assistant Examiner* — Kevin Everage
(74) *Attorney, Agent, or Firm* — Weide & Miller, Ltd.

(57) ABSTRACT

A vascular filter system and method are disclosed. In one embodiment, the filter system comprises a dispensing needle releasably attached to a filter dispenser which stores a length of filter wire. The filter wire dispenser has a guide tube which guides the filter wire into the needle and then into a vein during surgical implantation. The filter wire is configured to coil into a predetermined shape as it is deployed from the needle. The shape of the filter wire captures blood clots in the blood stream. The filter wire is configured with a perforated section and a non-perforated section. Perforations are in fluid communication with an inner hollow lumen in the filter wire. A hub assembly attaches to an end of the filter wire that is external to the body to provide a port into the lumen for application of medication into the lumen and out the perforations.

11 Claims, 10 Drawing Sheets

(56) References Cited

U.S. PATENT DOCUMENTS

| | | | |
|---|---|---|---|
| 2003/0208227 A1* | 11/2003 | Thomas | 606/200 |
| 2004/0158274 A1 | 8/2004 | WasDyke | |
| 2004/0193209 A1 | 9/2004 | Pavcnik et al. | |
| 2005/0131451 A1 | 6/2005 | Kleshinski et al. | |
| 2005/0159771 A1 | 7/2005 | Petersen | |
| 2006/0212127 A1* | 9/2006 | Karabey et al. | 623/23.75 |
| 2006/0229668 A1 | 10/2006 | Prestezog et al. | |
| 2009/0306703 A1 | 12/2009 | Kashkarov et al. | |

* cited by examiner

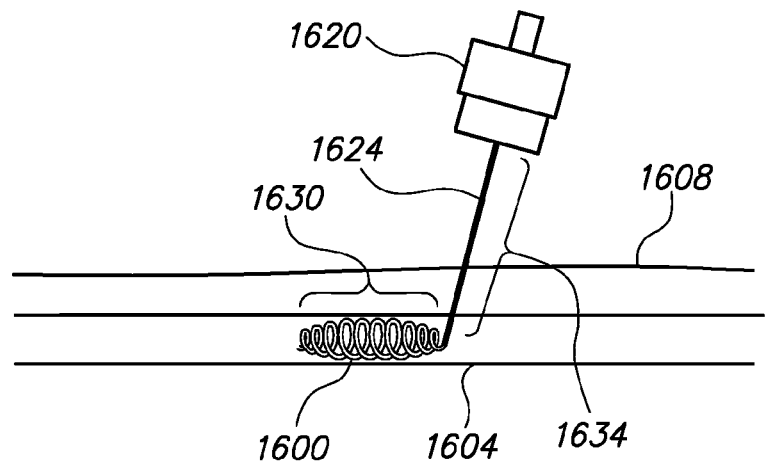
FIG. 20
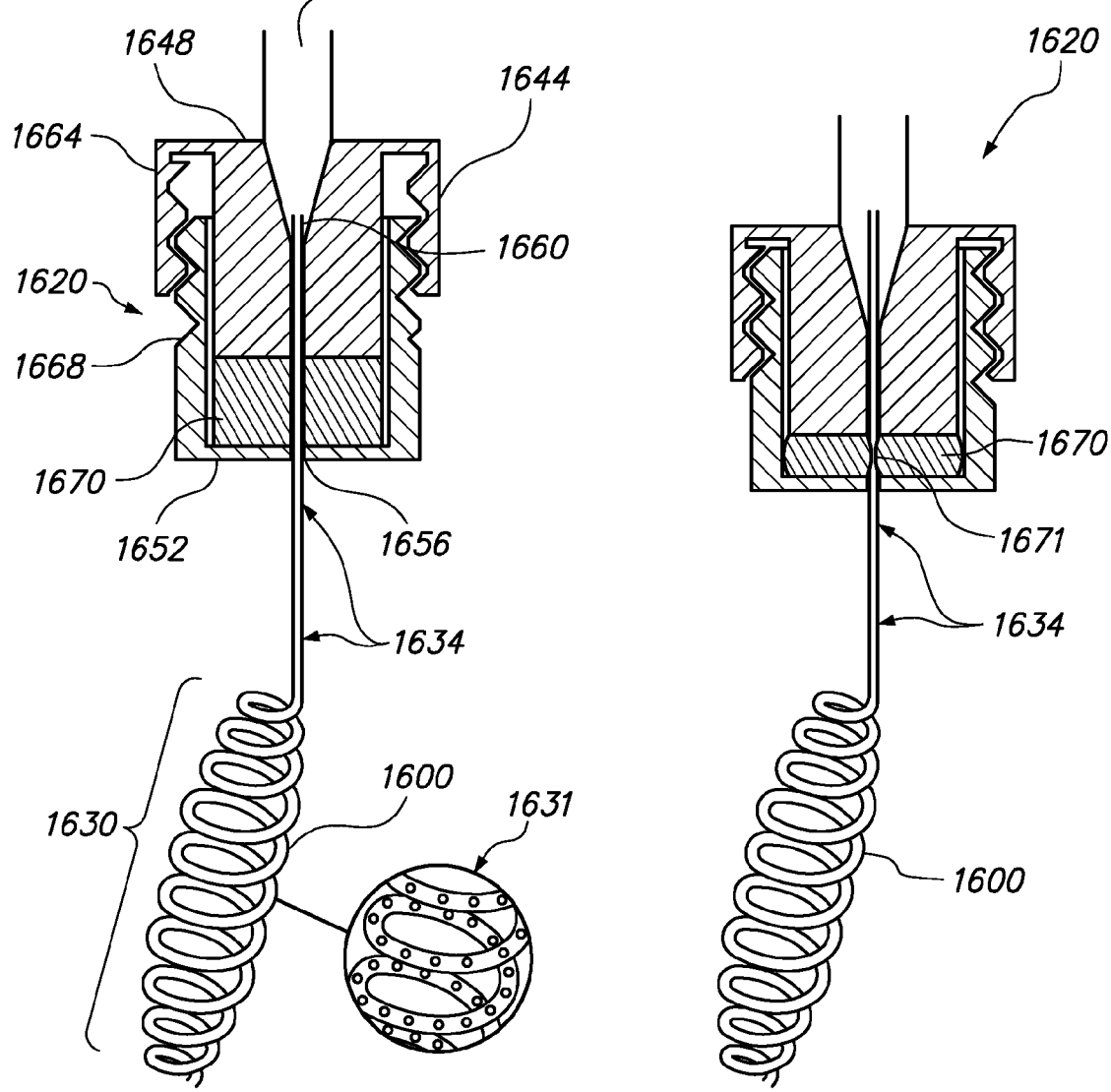
FIG. 21A  FIG. 21B

INTRAVENOUS FILTER WITH FLUID OR MEDICATION INFUSION CAPABILITY

CROSS-REFERENCE TO RELATED APPLICATIONS

This application claims priority to U.S. Provisional Patent Application No. 61/653,344 filed on May 30, 2012 titled IMPROVEMENT IN THE INTRAVENOUS DEEP VEIN THROMBOSIS FILTER AND METHOD OF FILTER PLACEMENT, and is a continuation in part of U.S. patent application Ser. No. 12/012,136 filed on Jan. 30, 2008 titled IMPROVED INTRAVENOUS DEEP VEIN THROMBOSIS FILTER AND METHOD OF FILTER PLACEMENT, which claims priority to U.S. Provisional Patent Application No. 60/898,939 filed on Jan. 31, 2007 titled IMPROVED INTRAVENOUS DEEP VEIN THROMBOSIS FILTER AND METHOD OF FILTER PLACEMENT.

BACKGROUND OF THE INVENTION

1. Field of the Invention

The present invention relates to vascular filters and, in particular to surgically implanted vascular filters which capture blood clots to prevent the clots from migrating to other regions of the circulatory system.

2. Related Art

Deep vein thrombosis (DVT) is a common problem and causes significant morbidity and mortality in the United States and throughout the world. DVT is caused when a blood clot forms in the deep veins of the legs. These blood clots typically occur due to slow or reduced blood flow through the deep veins such as when the patient cannot ambulate or otherwise efficiently circulate their blood. Another cause of inefficient circulation may be due to structural damage to the veins such as general trauma or subsequent to surgical procedures. Additionally, a blood clot may form in a deep vein due to a particular medical condition or a propensity for the patient to have a hypercoaguability state. For example, a woman on birth control who smokes has an increased risk of forming blood clots and is thus predisposed to DVT.

The result and clinical significance of DVT is when the clot breaks free from its location in the deep vein of the leg, the clot travels through the circulatory system and may eventually lodge in a location that is adverse to the patient's health. For example, the clot may dislodge from a location in the deep vein of the patient's leg and migrate through the heart and come to rest in the patient's lung causing a pulmonary embolism (PE) resulting in restricted circulation and can cause sudden death for the patient.

DVT & PE are currently prevented in several ways including anticoagulation therapy, thrombectomy, thrombolysis and inferior vena cava filter (IVC filter) placement. Anticoagulation therapy utilizes various medications that reduce the patient's propensity for forming blood clots. However, this form of therapy has the disadvantage that due to the patient's inability to form blood clots (due to the medication), there is an increased risk of excessive bleeding should the patient become injured, sustain surgical complications, or develop internal hemorrhaging.

Thrombectomy is a procedure generally performed for treatment of a PE, in which a blood clot is extracted from the vein using a surgical procedure or by way of an intravenous catheter and a mechanical suction device. This form of treatment is risky and technically very difficult because the catheter has to be steered or navigated to a specific location in order to extract the clot. Additionally, during a thrombectomy there is an increased risk of causing vascular damage due to the surgical procedure and use of various mechanical devices.

Thrombolysis is a medical technique that is performed for treatment of a PE, in which various medicines are infused into the region of the clot that subsequently causes the clot to dissolve. This form of treatment has the disadvantage that the medication may cause bleeding at other sites such as within the brain. For example, if a patient has previously had a minute non-clinical stroke, the medication used in a thrombolysis may cause a previously healed vessel to bleed within the patient's head.

IVC filter placement is usually conducted by surgically installing a filter in a large bore vein (such as the inferior vena cava) in the patient's upper abdomen. The IVC filter is placed using a large bore catheter (Introducer Catheter) for delivery of the filter. There are a couple of filters frequently used, those that are permanent and those that are removable, that may be placed using this technique. In the case where a removable filter is utilized, additional complications arise when the filter must be removed. The removable IVC filter is generally placed for a time period of a several weeks to a few months to prevent internal vascular scaring. However, removal of the IVC filter is technically challenging and requires large bore access. In practice, the removable IVC filter is captured by first accessing a large bore vein, using a large bore catheter to approach the filter, capturing the tip of the filter using a "snaring device" that is deployed through the large bore catheter, then pulling the filter into the catheter, and then the large bore catheter (with the filter therein) is removed from the patient. This procedure is very challenging, and requires increased patient recovery time.

Current IVC filter placement has several disadvantages such as increased costs, requires the use of special surgical procedures such as fluoroscopy or cardiology labs, requires a team (lab technician, nurse, and physician) of medical professionals, and requires a second substantially difficult surgical procedure for filter removal. Additionally, the IVC filter placement procedure requires that the patient's coagulation status be sufficient to withstand the surgical procedure. For example, if the patient has medical condition (liver failure) or is on medications that prevents their blood from clotting (i.e., using anticoagulation therapy) there is a substantial risk of excessive bleeding during the procedure. Also, existing IVC filter placement procedures are of questionable practicality for preventative placement because of the intrusive surgical procedures that must be performed to place the filter. Correspondingly, the risks (particularly filter removal) must be balanced between the need for the filter and the patient's ability to endure the surgical procedure.

As a result, there is a need in the art for a vascular filter that is inexpensive, facilitates placement by a physician at a convenient patient location (bedside), allows non-intrusive removal that can be performed at any location by either a physician or trained technician while having minimal recovery time and eliminating the need to determine the coagulation status of the patient. The method and vascular filter described herein enables a physician to place and remove the filter with minimal physical intrusion and at the same time reducing risk of procedural complications for the patient.

SUMMARY OF THE INVENTION

To overcome the drawbacks of the prior art and provide additional benefits and features, a vascular filter and method of filter placement is disclosed. In one embodiment, the vascular filter includes a dispensing needle releasably attached to a syringe and a filter wire dispenser. Generally, the needle has two ends, a delivery end and a coupling end. The delivery end is placed within a vein and allows filter wire to be implanted into the vein. The coupling end allows the needle to be releasably connected to a filter wire dispenser or syringe.

The filter wire dispenser stores a length of filter wire which is configured to coil upon deployment from the delivery end of the needle into a vein. The filter wire dispenser may store the filter wire as a spool or linearly, and includes a guide tube sized to insert into the needle. The guide tube is used to guide the filter wire from the dispenser into the needle.

The filter wire may be configured to coil upon deployment in a number of ways. One way is to put residual stresses, surface tensions, or both into the filter wire such that, once deployed, the filter wire will coil into a predetermined shape as defined by the stresses and surface tensions in the filter wire. The filter wire may be configured to coil into a vortex type, nested, or tangled web shape as desired. In addition, the filter wire of some embodiments may have a flexible tip to better prevent damage to the interior walls of a vein.

Once deployed a portion of the filter wire may be left protruding from the patient to allow the filter to be fixed in position. The protruding portion of the filter wire may be secured to a fixation device attached to the patient's skin. In one or more embodiments, the fixation device may have a portion configured to engage and secure the filter wire such as a protrusion.

The vascular filter, in one embodiment, is implanted by accessing a vein with a needle, attaching a filter wire dispenser storing a length of filter wire to the needle, and advancing the filter wire through the needle such that the filter wire exists the delivery end of the needle. In one or more embodiments, the filter wire has two ends, a first end and a second end. In one embodiment the first end of the filter wire exits the dispenser first. As the filter wire exits the needle into the vein, it begins to coil, as described above, to form a vascular filter.

Once the vascular filter is fully deployed the needle may be removed. In one or more embodiments, a portion of the filter wire is left protruding out of the patient so that it may be secured to a fixation device which generally covers the exist passage of the filter wire.

In some embodiments, proper access to a vein may be verified prior to implanting the filter. One way to verify that the needle is accurately located in a vein is to attach a syringe to the needle and draw blood from the vein to confirm the needle is indeed properly within the vein. The needle is improperly placed if no blood can be drawn. Once verified, the syringe may be removed from the needle while leaving the needle in the vein. A filter wire dispenser may then be attached and the filter wire implanted subsequently.

The vascular filter may be removed when desired or when no longer needed. In one embodiment, the vascular filter is removed by removing the filter wire from its associated fixation device and drawing the filter wire out of the patient. As the filter wire is drawn out of the patient, the filter wire unwinds itself so that it may be easily removed.

In one embodiment a vascular filter system as described herein is provided with medication infusion capability. In such an embodiment the filter wire is configured to coil within or around the filter wire dispenser and further configured for coiled deployment from the filter wire dispenser to a patient, the filter wire comprising an open first end connected to a hub assembly. The filter wire includes an inner lumen within the filter wire in fluid communication with the open first end. The filter wire also includes a perforated section and a non-perforated section. Two or more infusion ports are in the perforated section such that the two or more infusion ports are in fluid communication with the inner lumen of the filter wire. A hub assembly is at the open first end such that the hub assembly is configured to surround at least a portion of the non-perforated section of the filter wire and selectively open and close the inner lumen to control the flow of medication into the perforated portion of the filter wire.

In one configuration the infusion ports are holes in the perforated section of the filter wire which establish the inner lumen in fluid communication with the blood stream. The hub assembly may comprise a luer lock. In one embodiment the hub assembly is configured to mate with a syringe to accept an administration of medication into the inner lumen of the filter wire.

Also disclosed is a vascular filter system that includes a length of filter wire having a first end and a second end. In this embodiment the length further includes a non-perforated section at the first end with an opening at the first end that is part of an inner passageway within the filter wire. A perforated section connects the non-perforated section and the second end such that the perforated section is configured to coil to form a filter upon deployment from the delivery end of the dispensing needle. Also part of this embodiment are two or more perforations in the perforated section that are in fluid communication with the inner lumen. A hub assembly is releasable connected near the first end of the filter wire and is configured to selective open and close the inner lumen.

In on variation the vascular filter system further comprising a antithrombogenic on at least an outer surface of the perforated section. The portion of the filter wire that is within the hub assembly may be resilient.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The components in the figures are not necessarily to scale, emphasis instead being placed upon illustrating the principles of the invention. In the figures, like reference numerals designate corresponding parts throughout the different views.

FIG. 20 illustrates an infusible filter and associated hub assembly.

FIG. 21A illustrates a more detailed view of the infusible filter and hub assembly including a close up of the filter wire with infusing mechanism.

FIG. 21B illustrates the assembly of FIG. 21A with the compression element compressed to close the inner lumen of the view of the filter.

DETAILED DESCRIPTION OF THE PREFERRED EMBODIMENTS

In the following description, numerous specific details are set forth in order to provide a more thorough description of the present invention. It will be apparent, however, to one skilled in the art, that the present invention may be practiced without these specific details. In other instances, well-known features have not been described in detail so as not to obscure the invention.

One of the primary concerns regarding deep vein thrombosis (DVT) is that should the thrombosis (blood clot) dislodge from the original location, the clot may travel to another region of the circulatory system and cause injury and or death to the subject. For example, if a DVT dislodges it may migrate through the heart and eventually re-lodge in the lung of the subject thus causing a pulmonary embolism (PE) which prevents adequate circulation and can cause sudden death. By placing an intravenous filter in the common femoral vein, the blood clot is captured and prevented from migrating to vulnerable regions of the circulatory system. The filter may be placed in any vein or at any location such that the filter can capture a clot prior to causing damage to the patient. The term vein and vessel are used and defined interchangeable herein.

Figure 1:
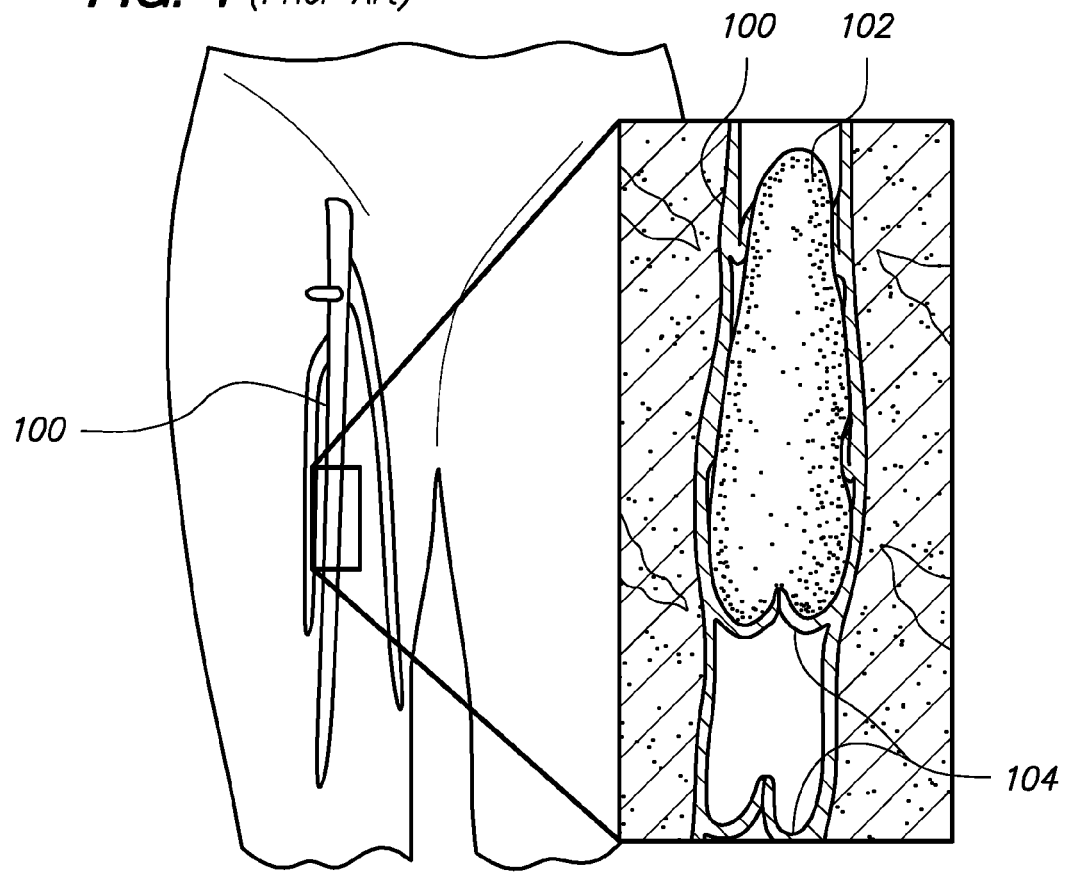
FIG. 1 illustrates a typical blood clot lodged within a femoral vein.

Referring now to the drawings, FIG. 1 illustrates a typical DVT where the common femoral vein 100 has a blood clot 102 lodged therein. As the blood clot 102 is formed there is reduced blood flow through the common femoral vein 100 because the blood clot begins to obstruct the fluid pathway. The reduced blood flow produces an environment that facilitates clot formation. In particular, as the blood flow is reduced, blood begins to coagulate in the chambers of the vascular valves 104 and as a result the blood clot 102 increases in size.

Figure 2:
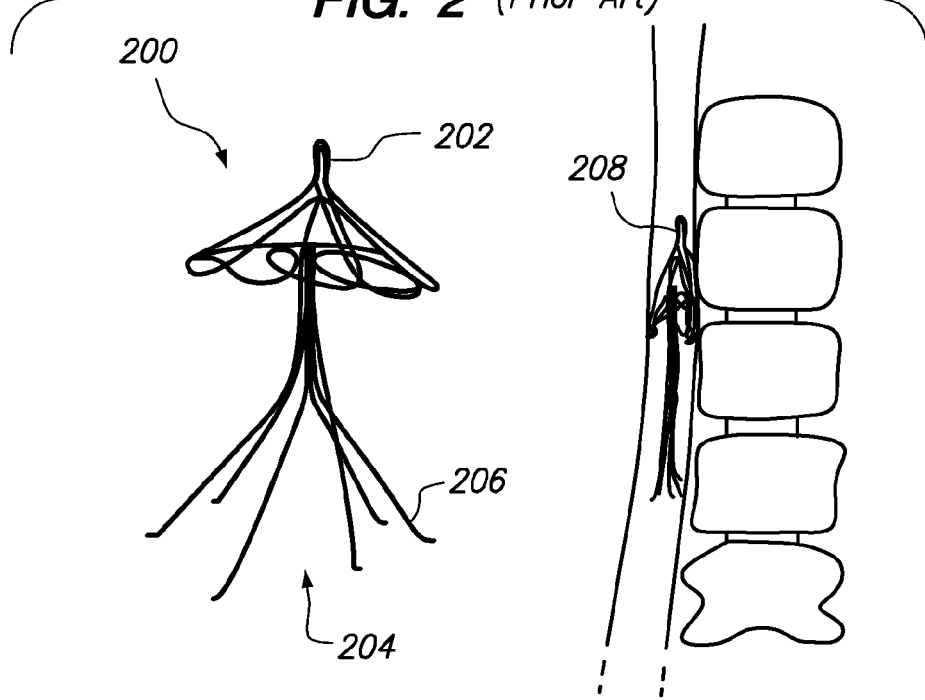
FIG. 2 illustrates an existing inferior vena cava filter and the proximate location of the filter in the upper abdomen.

FIG. 2 illustrates a known inferior vena cava vascular filter that is surgically implanted into the patient's upper abdomen. This inferior vena cava filter (IVC filter) 200 is commonly deployed using a large bore catheter and access to a large bore vein such as the inferior vena cava. The IVC filter 200 has a first end 202 and a second end 204 where the second end comprises a plurality of individual wire components 206. In the proximity diagram of FIG. 2, an IVC filter 200 is shown within the inferior vena cava at location 208 in the upper abdomen of a patient.

Figure 3:
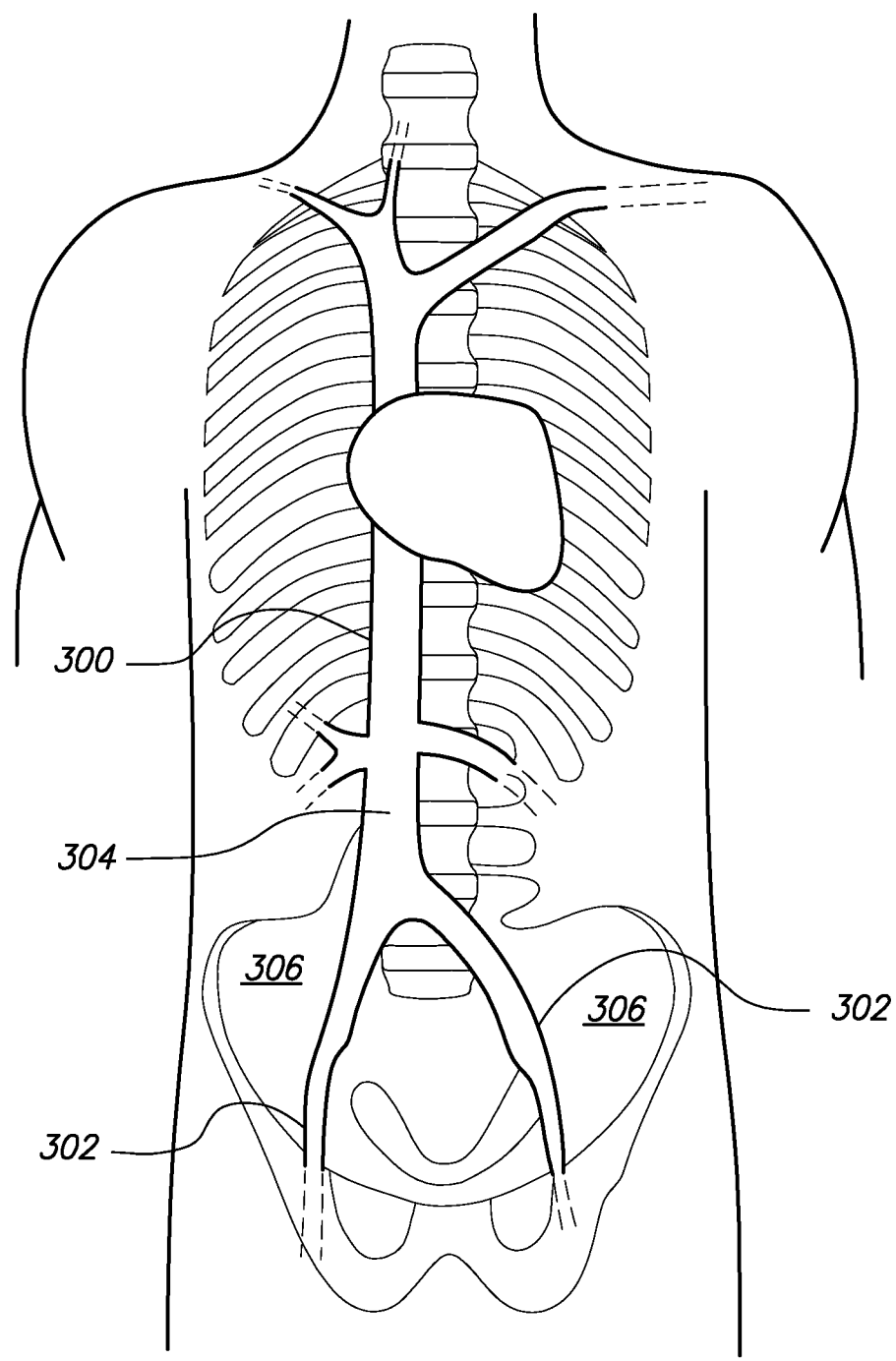
FIG. 3 illustrates the inferior vena cava and the two femoral veins.

FIG. 3 illustrates the inferior vena cava 300 and two common femoral veins 302 branching off the inferior vena cava. In the known use of intravenous filters such as the IVC filter discussed above, it is common to place the IVC filter within the inferior vena cava 300 at location 304 in the upper abdomen.

As stated above, placement of an IVC filter within the inferior vena cava 300 is expensive, requires special surgical procedures, requires imaging from a radiology or cardiology suite to ensure correct placement with the inferior vena cava, and is a substantially difficult and complicated surgery. In addition, known IVC filters must be placed in a large bore vein, and the placement surgery itself poses a significant risk in patients with conditions that prevent proper blood clotting.

The vascular filter of the present invention has several advantages over known filters. In contrast to the above, the vascular filter of the present invention may be placed within one of the common femoral veins 302. In addition, the vascular filter may be placed at any other location in the body which is suited to capture or retain blood clots. The vascular filter may be placed "blind" without imaging guidance from an expensive radiology or cardiology suite. Furthermore, the vascular filter may be placed in the common femoral vein 302 at hip level which is an area routinely used for catheter and other line access. Use of this common access area is another advantage in that such use of a commonly accessed area tends to reduce complexity and risk during placement as it is a well known access area.

Though placement at hip level has advantages, placement at hip level may not be ideal in all patients and thus the vascular filter may also be placed in other areas. For example, in one embodiment, the filter may be placed in the groin region 306 of the patient. It is contemplated that the vascular filter of the present invention may be placed where it is best able to capture a dislodged blood clot and that more than one filter may be placed to ensure that any dislodged blood clots are captured. For example, in one embodiment the vascular filter may be placed in both of the common femoral veins 302 should the patient's medical condition require filtration of both legs. In other embodiments, additional vascular filters may be placed as well.

Placement of the vascular filter begins by accessing a common femoral vein 302. Though the following description describes an embodiment of the present invention where the vascular filter is placed within a common femoral vein 302, the vascular filter may be similarly placed in other veins where dislodged blood clots may be captured as necessary.

Figure 4:
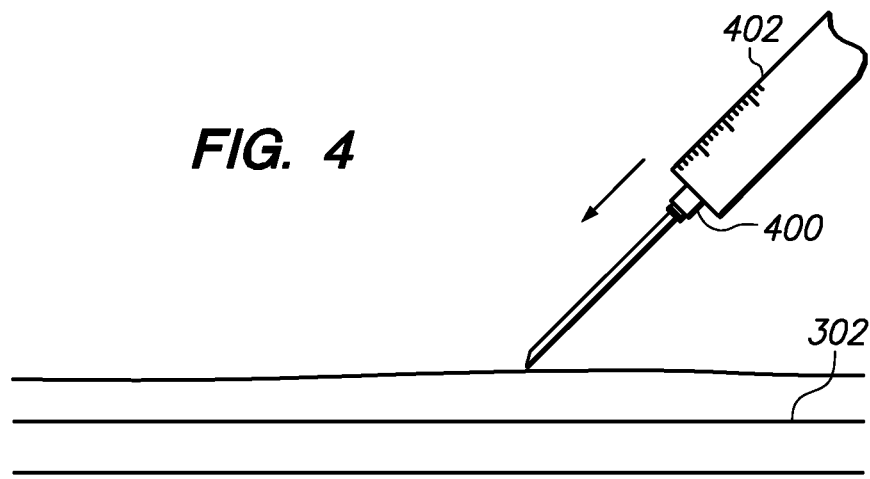
FIG. 4 illustrates a common femoral vein prior to access by a needle and syringe assembly.
Figure 5:
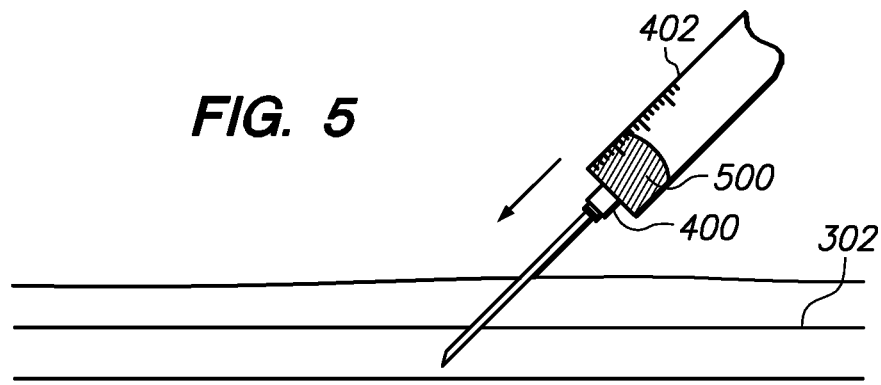
FIG. 5 illustrates actual needle and syringe assembly access into the common femoral vein.

FIGS. 4 and 5 illustrate a common femoral vein 302 accessed by a dispensing needle 400 and syringe 402 assembly. In one or more embodiments, the needle 400 has a first or delivery end through which a vascular filter is implanted in a patient, and a second or coupling end at which a syringe or filter dispenser may be attached. Notably, the coupling end in one or more embodiments may be configured to permit releasable attachment of the needle 400 as described further below.

Generally, proper access to the common femoral vein 302 may be verified by syringe aspiration (drawing blood from the vein into the body of the syringe) and is visually confirmed by blood return 500 into the syringe. In other embodiments, elements other than a syringe may be utilized including, but not limited to a single hollow large bore needle of which the blood can be seen flowing out of without syringe aspiration.

Figure 6:
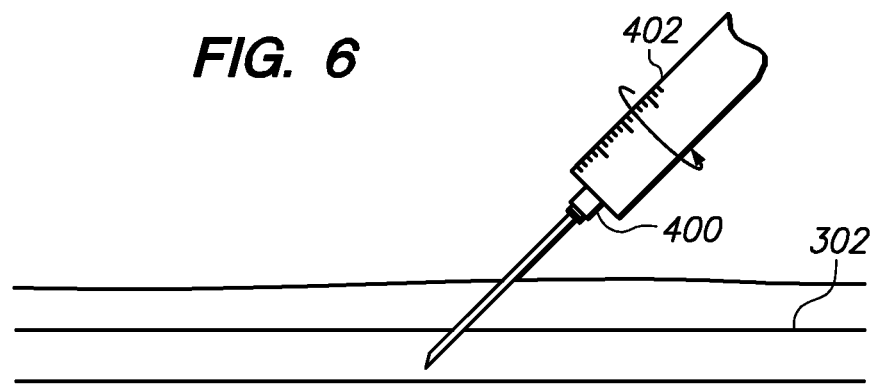
FIG. 6 illustrates removal of the syringe.

As illustrated in FIG. 6, the syringe 402 may be disengaged or removed from the needle 400 without removing the needle from the common femoral vein 302. In one or more embodiments, proper access to the common femoral vein 302 may be confirmed prior to disengaging the syringe 402 by inspecting the syringe for blood return. Such blood return confirms that the needle 400 is within a vein.

It is noted that disengagement or removal of the syringe 402 from the needle 400 may occur in various ways and that the syringe is releasably attached to the needle. For example, the syringe 402 may be fitted with a bayonet type of locking mechanism that retains the needle 400 within the end of the syringe. In addition, any other type of mechanism in addition to or other than a bayonet type locking mechanism may be utilized including but not limited to a manufactured threaded coupling system with "male and female" thread components. The locking mechanism may be any type of configuration that releasably retains the needle in the syringe and because these mechanisms are well known in the art they will not be described in detail so as not to obscure the present invention.

Figure 7:
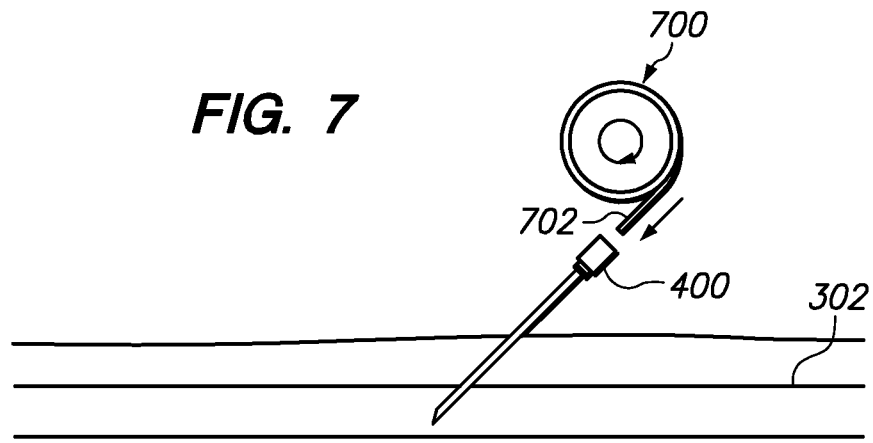
FIG. 7 illustrates attachment of the filter dispenser to the needle.

Attachment of the vascular filter dispenser 700 to the needle 400 is illustrated in FIG. 7. In one embodiment, the vascular filter dispenser 700 is a spool device that is configured to house and dispense filter wire housed with in the dispenser. The vascular filter dispenser 700 is fitted with a guide tube 702 that facilitates the deployment of the filter wire from the dispenser through the needle 400 and into the common femoral vein 302. It is contemplated that the end of the guide tube 702 be sized for operative insertion into the inner diameter of the needle 400. The guide tube 702 provides a smooth transition for the filter wire during the deployment process as the wire leaves the filter dispenser 700 and enters the needle 400. In some embodiments, filter means other than a wire may be utilized such as but not limited to monofilament strand or other materials with reformable properties. These structures may be preformed or shaped and/or configured at the time of use.

Figure 8:
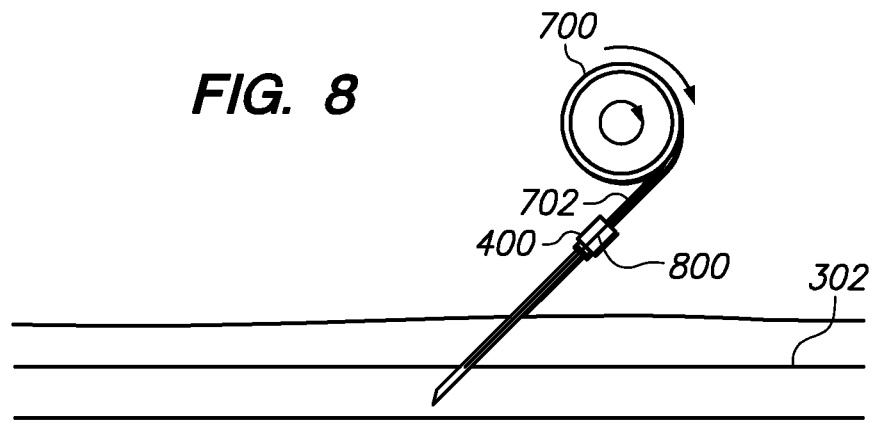
FIGS. 8 through 11 illustrate deployment of the vascular filter.

Reference is now made to FIGS. 8 through 11 individually and in combination for illustrating the deployment of the vascular filter. As shown in FIG. 8, a needle 400 and a vascular filter dispenser 700 are coupled together and the filter dispenser is actuated such that the filter wire 800 is fed from the dispenser through the needle and into the common femoral vein 302. In one embodiment, the filter dispenser 700 is actuated by a rotational movement of the dispenser so that the filter wire 800 is un-coiled and fed down the guide tube 702 and into the needle 400. It is contemplated that the filter dispenser 700 may comprise a user-rotatable wheel or knob in one or more embodiments. When rotated, the knob un-coils the filter wire 800 and feeds the same down the guide tube 702. The knob may un-coil the filter wire 800 through physical contact with the filter wire. However, it is contemplated that there may be an attached reel which is actuated by rotational movement of knob. Other embodiments of the filter dispenser 700 are contemplated such as a linear dispenser by which the filter wire is translated down the length of the dispenser and into the needle.

Figure 9:
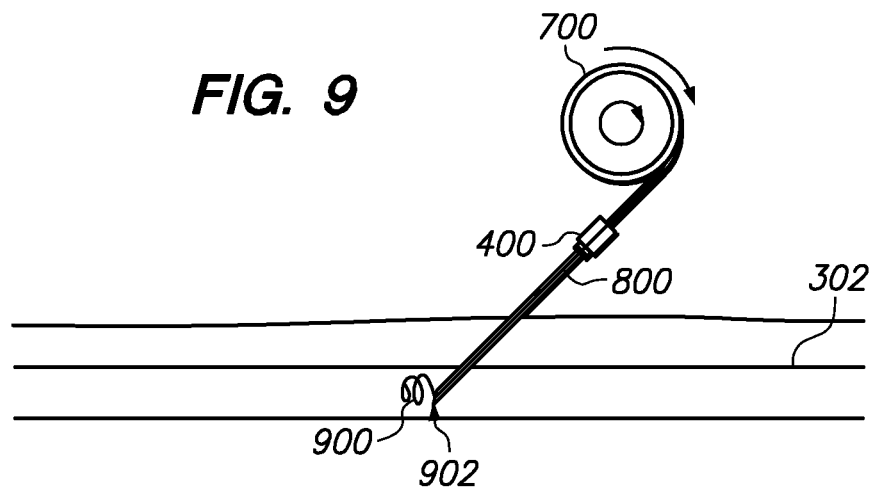

As best illustrated in FIG. 9, as the filter wire 800 traverses down the needle 400 it remains substantially straight. However, when the filter wire 800 exits the end of the needle 902, the filter wire begins to form a coil 900 within the common femoral vein 302. The filter wire coils due to residual stresses of the wire and the preformed shape memory imparted into the wire during the manufacturing process.

In one or more embodiments, the filter wire 800 has a first and a second end and is preferably fabricated from a suitable material such as titanium, Nitinol, or monofilament strand to name a few. The filter wire 800 may also be fabricated from polymer as well. The wire may be similar to known wires commonly used in the medical industry and, in one or more embodiments, may range in diameter from 0.015-0.035 of an inch. Additionally, the filter wire 800 may be treated with a compound that prevents clot formation on the wire such as a Heparin anticoagulation coating. The wire may comprise a mesh form or may be constructed of metal, plastic or a combination thereof or any other material. In addition, the filter wire 800 may have a very flexible tip at its first end to reduce the possibility of damaging the inside wall of a vein when the filter wire is implanted.

In one embodiment, an important characteristic of the filter wire 800 is that the wire be preformed to have residual stresses and/or surface tensions such that the wire will automatically coil once advanced beyond the delivery needle end 902. For example, the filter wire may be fabricated so that the surface tension along the length of the wire causes the wire to naturally coil unless otherwise constrained. In this way, the filter wire 800 may be housed or stored in one dispenser configuration and upon proper deployment; the filter wire would coil into a predetermined shape. In another embodiment, the filter wire may be preformed to take any various shapes that will achieve the goals set forth herein. For example, the filter wire may be preformed to have a vortex shape (coils of increasing/decreasing diameter) once deployed. Other embodiments may provide filter wire that is preformed to have a nesting or tangled web shape.

Figure 10:
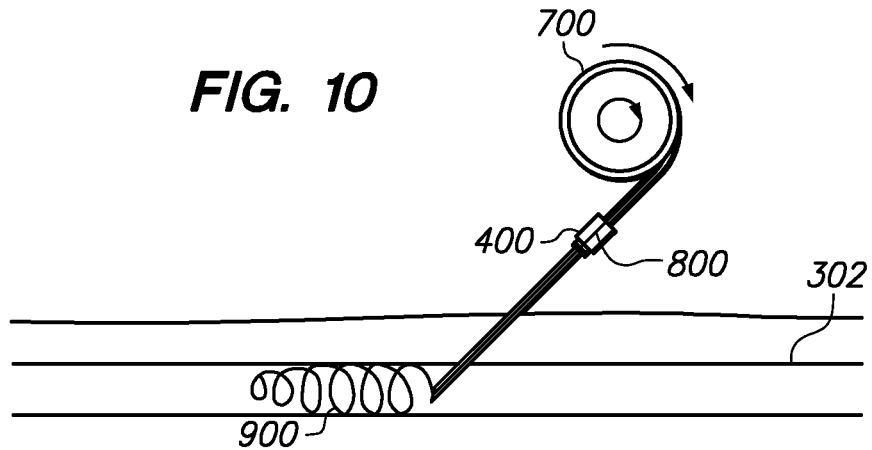
Figure 11:
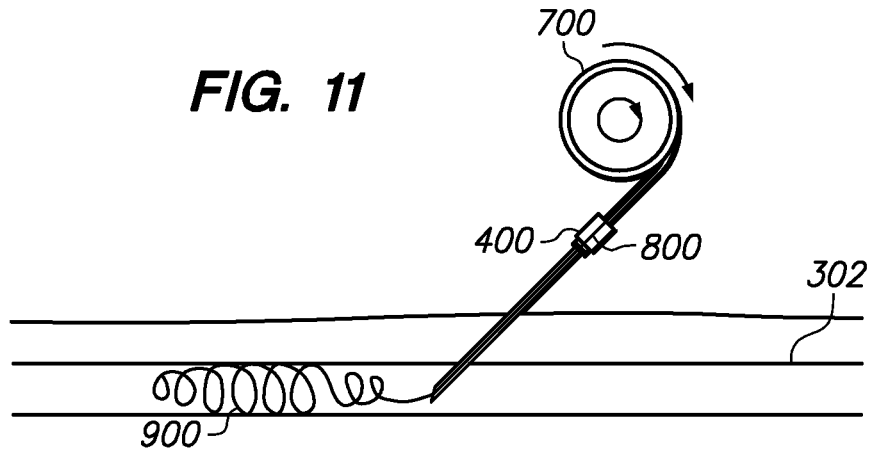

As illustrated in FIGS. 10 and 11, as the filter wire 800 is advanced into the common femoral vein 302, the coil becomes larger and longer such that a substantial coil of wire is formed within the vein. As a result, the coil 900 becomes a partial flow restriction within the common femoral vein 302 capable of capturing and retaining a blood clot therein.

Figure 12:
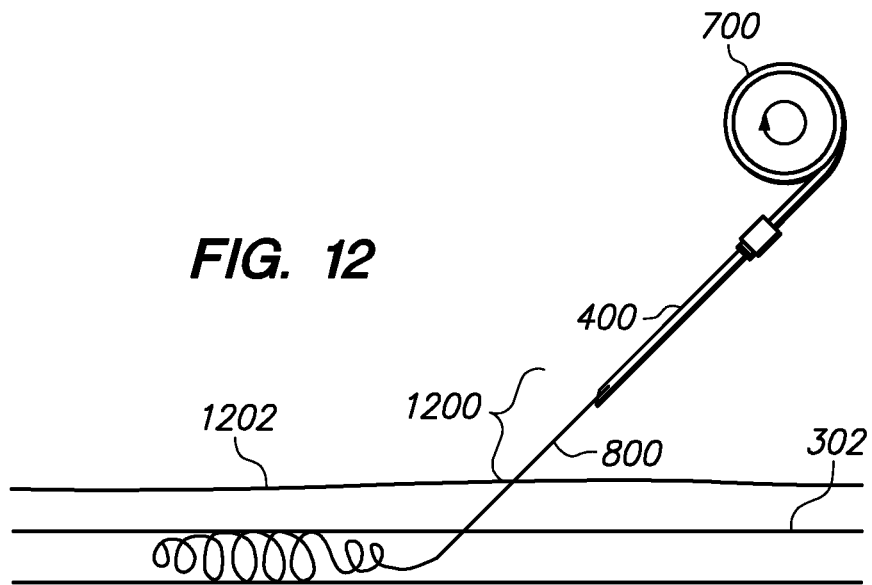
FIGS. 12 and 13 illustrate removal of the filter dispenser and needle.
Figure 13:
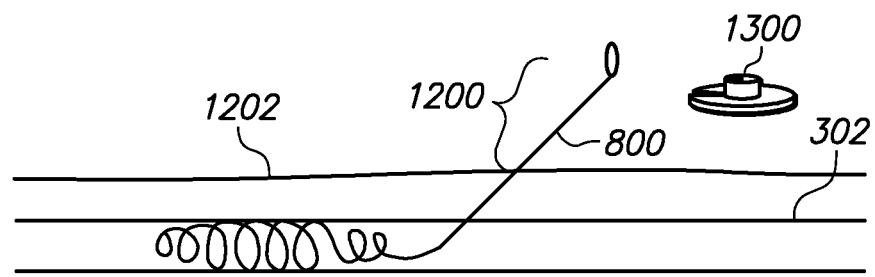
Figure 14:
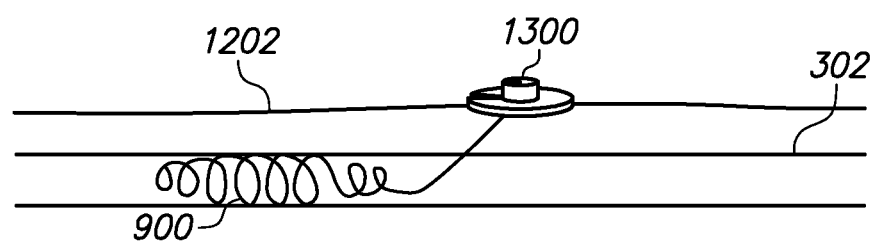
FIG. 14 illustrates retention of the filter wire to the patient's leg.

In FIG. 12, the filter wire 800 has been deployed and the filter dispenser 700 and delivery needle 400 are retracted from the subject's common femoral vein 302. As the dispenser 700 and needle 400 are removed, a portion 1200 of the filter wire 800 may be left protruding from the subject's skin surface 1202 so that it may be secured to a fixation device 1300 to prevent the filter wire 800 from moving within the vein. As illustrated in FIGS. 13 and 14, a portion 1200 of the filter wire 800 is intentionally left protruding from the subject's skin surface 1202 so that it may be looped and subsequently attached to a fixation device 1300. The fixation device 1300 is then secured using a medical dressing to the subject's skin 1202 and may cover the filter wire's exit. It is contemplated that types of fixation devices 1300 other than those illustrated in the figures may be used, and that in other embodiments the protruding portion 1200 of the filter wire 800 may be attached in other ways such as by tying or adhering the filter wire to the fixation device.

Figure 15:
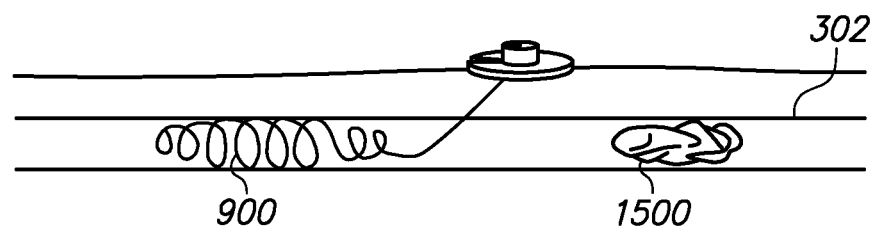
FIG. 15 illustrates a blood clot approaching the deployed vascular filter.
Figure 16:
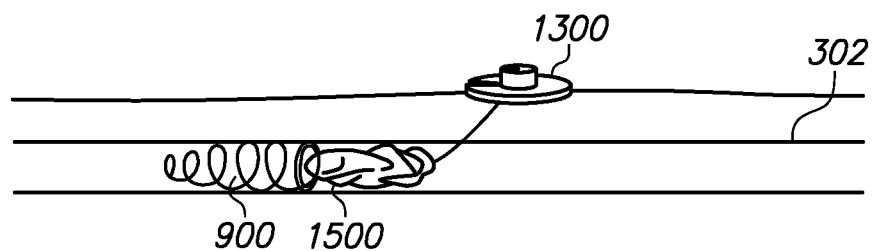
FIG. 16 illustrates the blood clot of FIG. 15 trapped by the vascular filter.

FIGS. 15 and 16 illustrate a blood clot 1500 approaching and being captured by the deployed vascular filter. As the blood clot 1500 migrates down the vein, it will encounter and preferably become trapped by the coil 900 of the vascular filter. As illustrated in FIG. 16, the blood clot 1500 will become lodged or entangled with the vascular filter's coils and in this way the clot is prevented from entering other regions of the subject's circulatory system.

In the event that a blood clot 1500 is captured by the vascular filter, the clot may be removed in one of several ways. First, the entangled blood clot 1500 may be verified using ultrasound or x-ray techniques. If there is a blood clot 1500, then the blood clot may be dissolved using anticoagulation therapy or any other means. If the blood clot 1500 does not dissolve in a timely manner, the attending physician may decide to perform additional procedures such as thrombectomy or thrombolysis to resolve the blood clot. In some cases, permanent placement of a standard IVC filter may be required where the blood clot does not dissolve.

Figure 17:
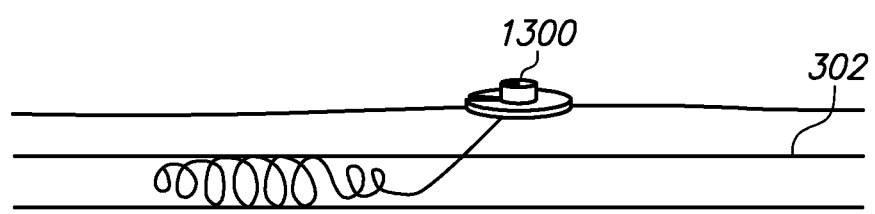
FIGS. 17 through 19 illustrate removal of the vascular filter.
Figure 18A:
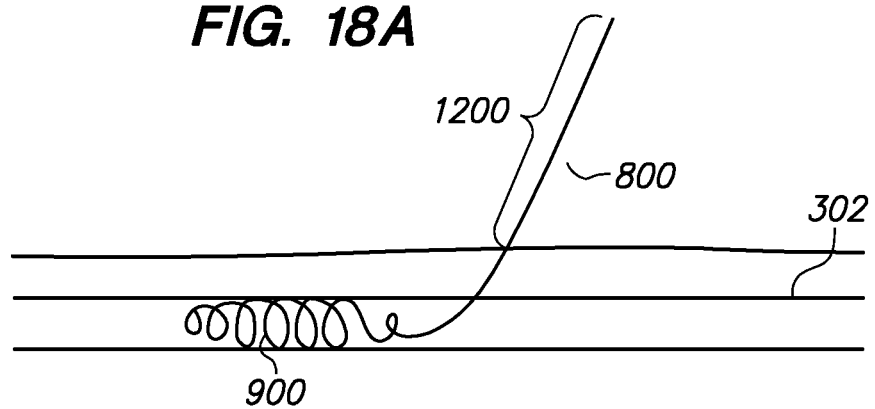
Figure 18B:
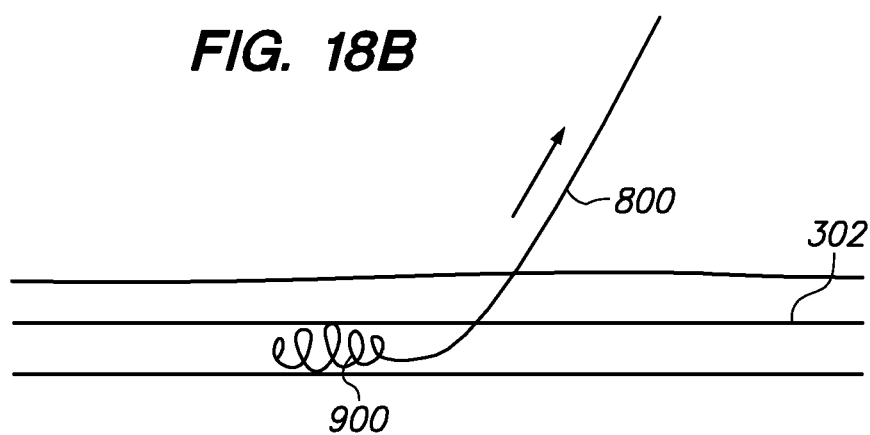
Figure 18C:
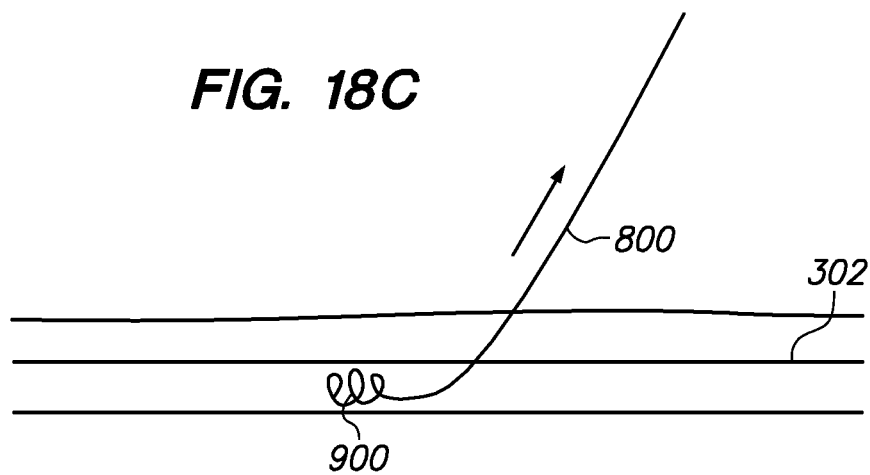
Figure 18D:
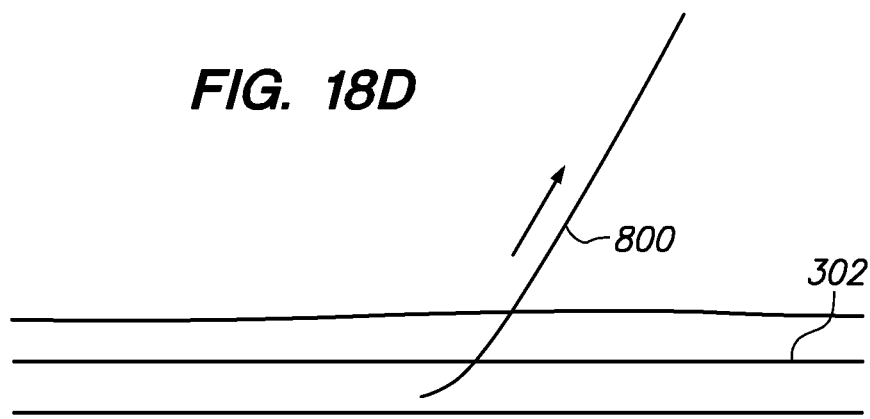
Figure 19:
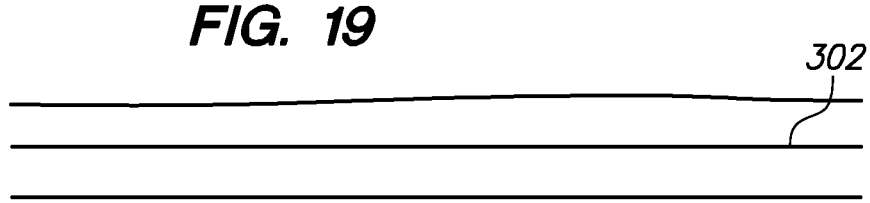

FIGS. 17 through 19 illustrate removal of the vascular filter. In FIG. 17, the fixation device 1300 and associated dressing are removed from the patient's skin surface 1202. Next, the protruding portion 1200 of the filter wire 800 is drawn away from the patient. As the filter wire 800 is drawn out of the patient, the filter coil 900 unwinds and/or unravels as illustrated in FIGS. 18a through 18d. A hydrophilic coating or hydrophilic filter wires 800 may be used, in one or more embodiments, to facilitate removal of the filter coil 900. Once the filter wire 800 is completely extracted from the patient as shown in FIG. 19, the vascular filter has been successfully removed and may be discarded.

The vascular filter disclosed herein has several advantages over known IVC filters. The new vascular filter is inexpensive and easily deployed/removed with minimal intrusion into the patient. In contrast, existing vascular filters require a complex and potentially risky deployment procedure which is very expensive, requires a team of medical professionals and the use of an operating room or cardiology suite. Additionally, existing vascular filters require an even more complicated and risky procedure for removal.

The new vascular filter is placed without the need for complex fluoroscopic guidance (i.e., the new filter is placed blindly). For example, unlike exiting filters that are placed within the inferior vena cava which requires x-ray fluoroscopic guidance for deployment, the new vascular filter may be placed without using any x-ray or imaging equipment.

The new vascular filter is minimally invasive and can be deployed at the patient's bedside or in an emergency room setting. Correspondingly, removal of the new vascular filter may be performed at a convenient location such as bedside.

The new vascular filter reduces the risk of complications because the filter is placed in a more conducive location within the patient's body. As disclosed herein, the new vascular filter may be placed in the pelvic or groin region of the patient unlike existing IVC filters which are generally placed in the upper abdomen or thoracic region. As a result, the new vascular filer is placed within one or both of the more accessible common femoral veins and is minimally intrusive for the patient. Another desirable aspect of the new vascular filter is a substantial reduction in recovery time for either deployment or removal of the new filter. In contrast, the existing filters require a substantial recovery time for both deployment and removal.

As an improvement to the filter and method of use described above, also disclosed is the filter configured as a route for infusion of fluids, gels, or medications through the filter and into the blood stream. The infused material may medicate the entire body or vascular system, or just the area of the filter. As such treatment can be directed to a very direct and focused area of the body or arterial system. As discussed above, the filter may be used to retain clots and as such, while the clot is retained within the filter, medication may be applied or infused through the filter as disclosed below to target the retained clot. This provides the benefit of concentrating the medication to the clot which is particularly useful for application of clot dissolving medication such as, but not limited to, Tissue Pasminogen Activator (TPA-Alteplase). In addition, it is also contemplated that medication may be infused through the filter as described below to prevent clotting of the blood around or onto the filter, or any other type of build-up of material or growth on the filter. This extends the effective life of the filter within the body and increases the ease of removal.

FIG. 20 illustrates an infusible filter and associated hub assembly. As discussed above, the filter 1600 is located within the vascular system, such as vein 1604 located below the surface of the skin 1608. A hub attachment 1620 connects to the externally located end 1624 of the filter 1600. The base function of the filter 1600 operates as described above and in connection with FIGS. 1-19. In this embodiment the filter 1600 including the externally located end 1624 includes an inner passageway that is configured to conduct medication or other material such as a liquid or gel. The passageway may comprise a lumen.

The filter wire maybe categorized into a perforated section 1630 which is contained within in the vascular system. The filter wire also includes an un-perforated section 1634 that connects the perforated section 1630 at a distal end and to the attachment hub at the proximal end. The perforated section has one or more openings (shown in FIG. 21) through which the medication or other material may exit the filter. The number and shape of the openings may be varied to meet the requirements of the filter, medication, and particular medical application.

The filter sections 1630, 1634 includes a passage between an open end at the hub attachment 1620 and the perforations (not shown in FIG. 20) for the movement of the medication or other material into the filter, through the filter, and out of the perforations. The hub attachment 1620, the structure of which is discussed below in connection with FIG. 21, serves several purposes and functions. The hub attachments provides an access port to the internal passage within the filter sections 1630, 1634 to thereby provide an input port for the medication or other material. The hub attachment 1620 also provides a clamping or compression element to open and close the opening into the internal passage of the filter. This controls the flow of medication or other material into and output of the internal passage. The hub attachment 1620 also provides an attachment point and structure to attach a syringe, drip line, medication storage/dispensing device infusion pump, or any other element configured to deliver medication or other material to the filter.

FIG. 21A illustrates a more detailed view of the infusible filter and hub assembly including a close up of the filter wire with infusing mechanism. This is but one possible configuration of the filter and hub assembly. It is contemplated that in other embodiments other configurations may be realized without departing from the claims that follow. For example, different medical applications may require that the disclosed and claimed device interface with other medical devices and as such modifications may be made to the device shown without departing from the scope of the invention and claims.

As shown generally, the filter includes hub attachment 1620 and the filter wire 1600. A non-perforated section of the filter wire connects the perforated filter section to the hub assemble. The filter may be made from any type material that is configured to perform as described herein.

A fluid chamber 1640 configured to connect to the hub assembly, which in this embodiment is a luer lock 1644. The fluid chamber 1640 contains medication or other material which is provided to the filter 1600 and ultimately to the patient. The fluid chamber may be part of a syringe, drip-line, infusion pump or medication administration device or any other element configured to store and connect to a hub assembly. The fluid chamber 1640 may permanently connect to the filter or may be selectively connectable and removable to apply medication or other material to the filter.

Configured to mate with or connect to the fluid chamber 1640 is a luer lock 1644 having a first end 1648 with an opening configured to mate with the external shape of the fluid chamber 1640, in this embodiment a tapered end. The hub attachment 1620 assembly is an addition to the prior art as it allows wire placement, such as for example, through a needle with the eventual needle removal. Once the entry needle is removed the hub assembly 1620 can be applied to the portion of the filter that is external to the body for infusion.

The luer lock 1644 is generally known in the art and not describe in detail herein. As shown the luer lock 1644 has an internal passageway or lumen from the first end 1648 to a second end 1652. In the second end 1652 is an opening 1656 configured in size and shape to accept a proximal end 1660 of the non-perforated section 1644 filter wire. The opening extends toward the proximal end of the luer lock 1644 to a establish fluid (or there material state) passageway with the fluid chamber 1640. Through this fluid passageway medication or other material may be provided to the filter wire 1600. The medication or other material may be pressurized in the fluid chamber 1640 to establish flow into the lower pressure filter wire. The pressure may be established by a syringe or gravity, or any other force to move the medication or other material from the chamber 1640 to the filter wire.

The luer lock 1644 also includes an outer ring 1664 with internal threads which rotationally interact with an externally threaded inner frame 1668 of the lure lock. Through rotational movement of the outer ring 1664 relative to the inner frame 1668 the outer ring moves in the linear direction between the proximal end 1648 and the distal end 1652.

The movement of the outer ring 1664 relative to the inner frame 1668 crushes an compression element 1670 that when crushed closes the passage between the chamber 1640 and the internal passageway in the filter 1600. The compression element 1670 may comprise any material capable of performing as described herein. The compression element 1670 is a known structure in the luer lock 1646 and it may also be known to pinch or otherwise close the flow of medication or other material into the filter 1600.

In one configuration the non-perforated section 1634 of the filter in contact with the compression element 1670 may comprise a different material or configuration than the portion of the filter not in contact with the compression element. For example, the non-perforated section 1634 of the filter in contact with the compression element 1670 may be flexible and resilient to return to shape after opening, while the perforated section 1630 may comprise a more stiff material capable of functioning as described above as a filter in a vascular environment.

FIG. 21B illustrates the assembly of FIG. 21A with the compression element compressed to close the inner lumen of the view of the filter. As shown the outer ring 1664 is twisted relative to the inner frame 1668 to compress (shown at element 1671) the compression element 1670, which in turn compresses the inner passageway or lumen to stop the flow of medication or other material.

Figure 22:
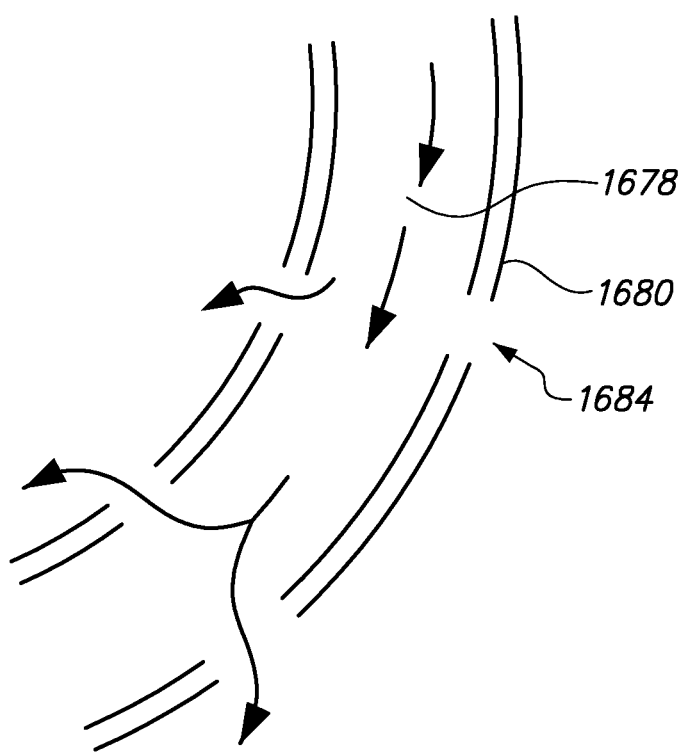
FIG. 22 illustrates a close up view of the perforated section of filter wire with medication outflow holes.

Also shown in FIG. 21A is a close up view 1631 of the perforated section 1630 of the filter. Each of the dots in the coiled filter wire comprise opening or holes through which the medication or other material may pass into the blood steam FIG. 22 illustrates a more detailed version of the filter. As shown the perforated section 1630 of the filter includes an outer wall 1680 which forms an inner passage 1678 or lumen through which medication or other material may flow or be placed. Perforating through the wall 1680 are openings 1684 which provide passages for the medication or other material to exit the inner passageway 1678 or lumen and enter the bloodstream. The openings 1684, which may referred to herein as infusion pores or diffusion pores, may be of any various size and shape and such size and shape may depend on the medication or other material, dosing requirements, patient condition or numerous other factors.

This current improvement allows the place filter to be a route of infusion for fluids and/or medication. The enhanced filter with infusion capabilities can therefore aid in patient care as an extra source of venous access, provides an additional means to protect the filter itself from developing blood clots and potentially will provide a means of breaking up or dissolving the trapped clot via infusion of clot dissolving medications including but not limited to Tissue Plasminoge Activater (TPA) and any other medication now existing or develop in the future.

In summary, once the filter has been placed medication can be infused directly into the blood stream via the inner lumen and multiple infusion pores (openings) located on the intravenous portion of the filter wire. In order to channel fluid through the inner lumen of the filter coil a custom coupling apparatus is provided to attach to a syringe or other device configured to present the medication into the inner passage of the filter wire. The coupler, such as hub assembly, allows for the filter wire with the open inner lumen to be put into fluid communication with a standard IV drip system or other medication administration mechanism via a luer lock connection (hub assembly). Within the coupler is a compression seal (4). When the two coupler bodies are threaded together the compression seal is deformed thus creating a fluid tight seal around the filter wire. Once a seal is made the coupler can be connected to an IV line allowing fluid to pass through the filter wire and infuse into the patient's blood stream.

It is further contemplated that various coating can be added to the surface of the filter to enhance its biocompatibility or prevent/inhibit growth or development of unwanted surface tissue by the body on the filter. An example is an antithrombogenic antiplatelet coating or material to prevent development thrombi in vitro. This may further prevent or reduce development of clots or scar tissue development on the vascular filter.

While various embodiments of the invention have been described, it will be apparent to those of ordinary skill in the art that many more embodiments and implementations are possible that are within the scope of this invention. In addition, the various features, elements, and embodiments described herein may be claimed or combined in any configuration or arrangement.

What is claimed is:

1. A vascular filter system with medication infusion capability comprising:
    a dispensing needle having a delivery end and a filter wire dispenser connection end; and
    a filter wire dispenser for storing a length of filter wire, wherein the filter wire dispenser comprises a guide tube, the guide tube sized for connection to the filter wire dispenser connection end of the dispensing needle;
    filter wire configured to coil within or around the filter wire dispenser and further configured for deployment from the filter wire dispenser to a patient, the filter wire comprising:
        an open first end connected to a hub assembly;
        an inner lumen within the filter wire in fluid communication with the open first end, the filter wire also including a perforated section and a non-perforated section;
        two or more infusion ports in the perforated section, the two or more infusion ports in fluid communication with the inner lumen of the filter wire; and
    a hub assembly at the open first end, the hub assembly configured to surround at least a portion of the non-perforated section of the filter wire and selectively open and close the inner lumen to control the flow of the medication into the perforated portion of the filter wire; and
    wherein the hub assembly is configured to mate with a syringe to accept an administration of medication into the inner lumen of the filter wire.

2. The vascular filter system of claim 1, wherein the length of filter wire includes residual stresses, surface tensions, or both configured to coil the length of filter wire into a predetermined shape.

3. The vascular filter system of claim 1, wherein the infusion ports are holes in the perforated section of the filter wire which establish the inner lumen in fluid communication with the blood stream.

4. The vascular filter system of claim 1, wherein the hub assembly comprises a luer lock.

5. A vascular filter system comprising:
- a dispensing needle, the dispensing needle having a delivery end and a coupling end;
- a length of filter wire having a first end and a second end, the length further including:
  - a non-perforated section at the first end with an opening at the first end that is part of an inner passageway within the filter wire;
  - a perforated section connecting the non-perforated section and the second end, a perforated section configured to coil to form a filter upon deployment from the delivery end of the dispensing needle;
  - two or more perforations in the perforated section that are in fluid communication with the inner lumen;
- a hub assembly releasably connected near the first end of the filter wire configured to selectively open and close the inner lumen;
- a filter wire dispenser for storing the length of filter wire, the filter wire dispenser having:
  - a storage housing configured to store the filter wire prior to dispensing in a patient;
  - a coupling end configured to releasably attach to the coupling end of the dispensing needle;
  - a guide tube between the storage housing and the coupling end configured to guide the filter wire from the storage housing to the coupling end; and
- wherein the hub assembly is configured to mate with a syringe to accept an administration of medication into the inner lumen of the filter wire.

6. The vascular filter system of claim 5, wherein the hub assembly comprises a luer lock.

7. The vascular filter system of claim 5, wherein the length of filter wire includes residual stresses, surface tensions, or both configured to coil the length of filter wire into a predetermined shape.

8. The vascular filter system of claim 7, wherein the predetermined shape consists of one of the following shapes: a helix shape, a vortex shape, a nested shape, and a tangled web shape.

9. The vascular filter system of claim 5, further comprising an antithrombogenic on at least an outer surface of the perforated section.

10. The vascular filter system of claim 5, wherein the length of filter wire is stored linearly within the filter wire dispenser.

11. The vascular filter system of claim 5, wherein a portion of the filter wire that is within the hub assembly is resilient.

* * * * *